United States Patent [19]

Kanno et al.

[11] Patent Number: 4,865,018
[45] Date of Patent: Sep. 12, 1989

[54] CONTROL APPARATUS FOR ENDOSCOPES

[75] Inventors: Masahide Kanno; Katsuyuki Saito; Akihiko Miyazaki, all of Tokyo, Japan

[73] Assignee: Olympus Optical Co., Ltd., Tokyo, Japan

[21] Appl. No.: 238,180

[22] Filed: Aug. 30, 1988

[30] Foreign Application Priority Data

Sep. 3, 1987 [JP] Japan ................................ 62-221359

[51] Int. Cl.[4] ............................................... A61B 1/04
[52] U.S. Cl. ........................................... 128/6; 358/98
[58] Field of Search ........................... 128/4, 6; 358/98

[56] References Cited

U.S. PATENT DOCUMENTS 4,667,230 5/1987 Arakawa et al. ..................... 358/98
4,759,346 7/1988 Nakajima ................................ 128/6
4,774,568 9/1988 Matsuo ................................. 358/98

Primary Examiner—William H. Grieb
Attorney, Agent, or Firm—Stevens, Davis, Miller & Mosher

[57] ABSTRACT

In a control device for endoscopes in which a fiber scope having an image guide and an electronic scope having a solid state imaging device can be selectively connected thereto, there are provided a control device for controlling many kinds of functions of these endoscopes, a selecting device for indicating the kind of selected endoscope, selectively making the control device in accordance with the functions of the endoscope indicated by the indicating device operative, and making the rest of the control devices inoperative, an adjusting device for adjusting the operational conditions of the various kinds of functions, and an indicating device for indicating the operational conditions of the various kinds of functions which are adjusted by the adjusting devices, and the control device for endoscope is arranged that only the adjusting devices for adjusting the operational conditions of the functions corresponding to the functions selected by the selecting device are made operative and the operational conditions of the selected functions are indicated in a mutually distinguishable manner from the operational conditions of the non-selected functions on the indicating device.

12 Claims, 9 Drawing Sheets

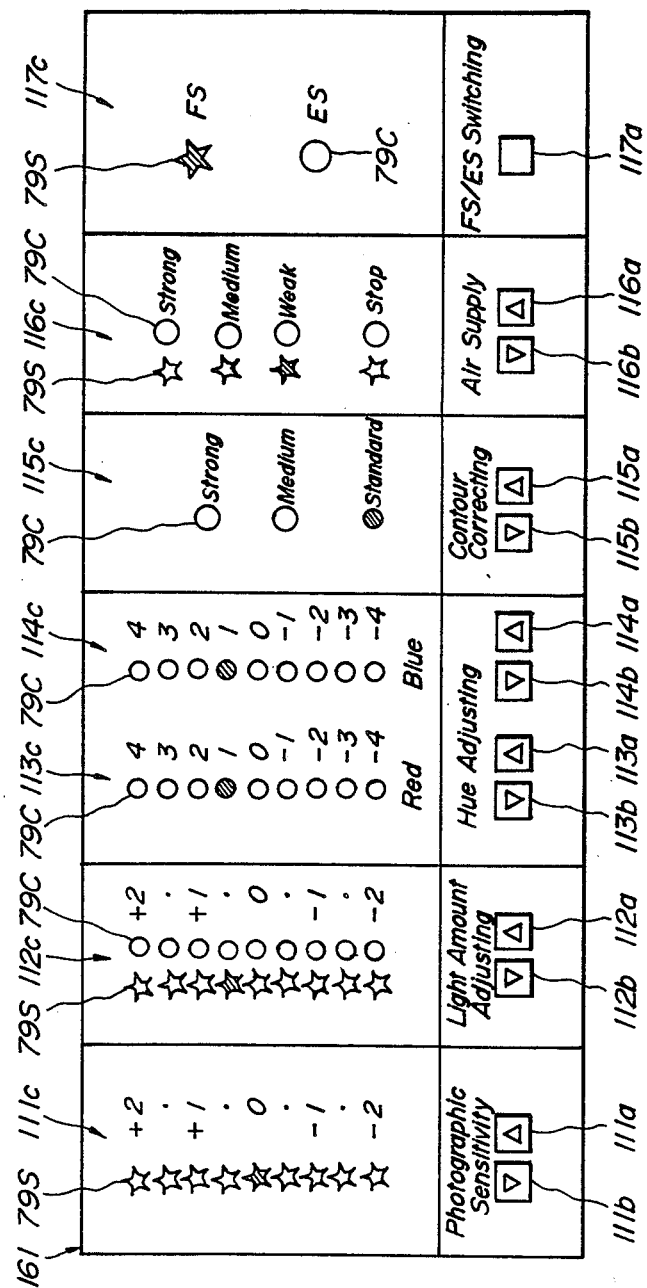

CONTROL APPARATUS FOR ENDOSCOPES

BACKGROUND OF THE INVENTION

Field of the Invention and Related Art Statement

The present invention relates to a control apparatus for endoscopes in which plural kinds of endoscopes having different functions can be controlled.

Heretofore, endoscopes (which are called fiber scopes) by which internal organs of living body can be observed by inserting a long and thin inserting portion thereof and medical treatments and cures can be taken by using a medical appliance inserted in a medical appliance channel at need are widely used.

Various kinds of electronic scopes in which a solid state image sensor, for example, charge coupled device (CCD), is used as an imaging means are also suggested. This electronic scope has such advantages that the resolution thereof is higher than that of the fiber scope, it is easier to record and reproduce the image and to make an image processing such like making the image enlarge or comparing two images.

There are two imaging systems in order to image a colored image obtained by said electronic scopes, one of which is a field or frame sequential system by which the illuminating lights are successively changed to R (red), G (green), B (blue), etc., and other one of which is a color mosaic system (simultaneous system) in which there is provided a filter array, wherein colored filters through which the color of R, G, B etc. passes are arranged in mosaic, in front of the solid state image sensor. The electronic scope using the field or frame sequential system has an advantage that it is possible to make the number of pixels small in comparison with the color mosaic system. On the other hand, the electronic scope sing the color mosaic system has an advantage that no color deviation occurs.

Since each of these electronic scopes has an illuminating systems different from each other, it was necessary to prepare light source apparatuses for each scopes. Thus, the applicant of the present application has suggested a light source apparatus for endoscopes which can be commonly used in the electronic scope having an imaging means using a field or frame sequential system, the electronic scope having an imaging means using a color mosaic system and the fiber scope in Japanese Patent Application No. 62-34,028. By using this light source apparatus, it is possible to operate the three kinds of scopes by only one light source apparatus, so that the economical efficiency thereof can be elevated.

In such light source apparatus which can be commonly used in the fiber scopes and the electronic scopes, the operating panel thereof has such a structure as illustrated in FIG. 1.

In FIG. 1, there is indicated an operating panel 1 of the light source apparatus having functions for adjusting the photographic sensitivity, the amount of light, hue of red and blue color and air supply and for correcting the contours. There are provided a sensitivity increasing switch 2a, a sensitivity decreasing switch 2b and an indicator 2c for adjusting the photographic sensitivity, an increasing switch 3a, a decreasing switch 3b and an indicator 3c for adjusting the amount of light, an increasing switch 4a, a decreasing switch 4b and an indicator 4c for adjusting the red hue, an increasing switch 5a, a decreasing switch 5b and an indicator 5c for adjusting the blue hue, an increasing switch 6a, a decreasing switch 6b and an indicator 6c for correcting the contour and an increasing switch 7a, a decreasing switch 7b and an indicator 7c for adjusting the air supply. In each indicators 2c, 3c, 4c, 5c, 6c and 7c, an operational mode of each adjusting and correcting functions is indicated by lighting one and light emitting diodes (hereinafter it is said as LED) arranged thereon. It should be noted that the indicators denoted by oblique lines in figures show the LEDs 9 in lighting.

Out of said adjusting and correcting functions, the function for adjusting the photographic sensitivity is used only for the fiber scope, the functions for adjusting the hue and correcting the contour are used only for the electronic scopes, and the functions for adjusting the amount of light and air supply are used for both scopes.

As described above, what functions should be used depends on the scope to be used. However, there is no indication by said switch and LEDs 9 to distinguish which function for fiber scope or electronic scope is used on this operating panel 1. And since LEDs in the indicators 4c and 5c for adjusting the hue and 6c for correcting the contour are lighted also during the fiber scope is used, and the LEDs 9 in the indicator 2c for adjusting the photographic sensitivity is lighted also during the electronic scope is used, there is a danger of mis-operating. For example, there is a danger such that during the fiber scope is used an operator might put on the switches 4a or 4b for adjusting the hue in error by way of changing the photographic sensitivity. And contrary, there is a danger such that during the electronic scope is used an operator might put on the switches 2a or 2b for adjusting the photographic sensitivity by way of changing the hue. And, in case that the operator does not mistake, there still remains such dangers that the operator would be confusing and could not establish the desired operational mode promptly.

SUMMARY OF THE INVENTION

The present invention has for its object to provide a control apparatus for endoscopes in which it is possible to control plural kinds of endoscopes having different functions, mis-operations can be prevented and the operating efficiency can be elevated.

The control apparatus for endoscopes according to the present invention comprises:

a controlling means for controlling plural kinds of functions which are at least partially different for each of said plural kinds of endoscopes;

a selecting means for selecting at least one function to be controlled out of said plural kinds of functions in accordance with an endoscope connected to said control apparatus;

an adjusting means for adjusting an operational condition of said function selected by said selecting means; and an indicating means for indicating the operational condition of said function selected by said selecting means so as to be able to distinguish said function from at least one function which is not selected by said selecting means.

BRIEF DESCRIPTION OF THE DRAWINGS

FIG. 10 is a schematic view showing a panel of a light source device according to a fifth embodiment of the present invention.

DETAILED EXPLANATION OF THE PREFERRED EMBODIMENTS

Figure 1:
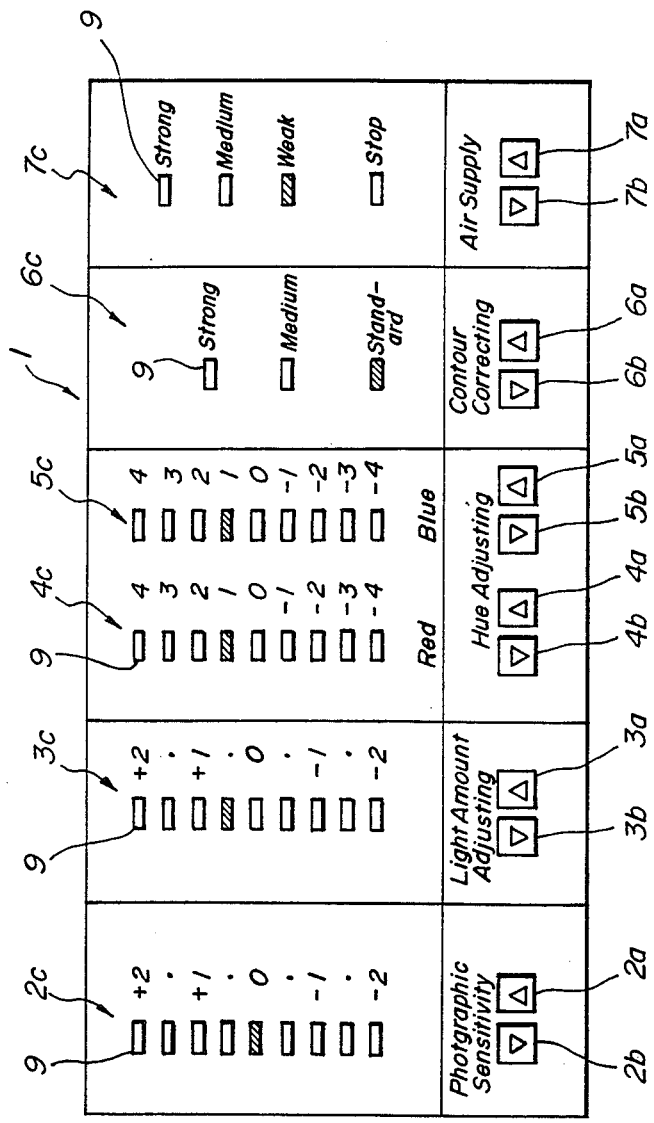
FIG. 1 is a schematic view showing the operating panel of the conventional light source apparatus which can be commonly used in the fiber scope and the electronic scope.
Figure 2:
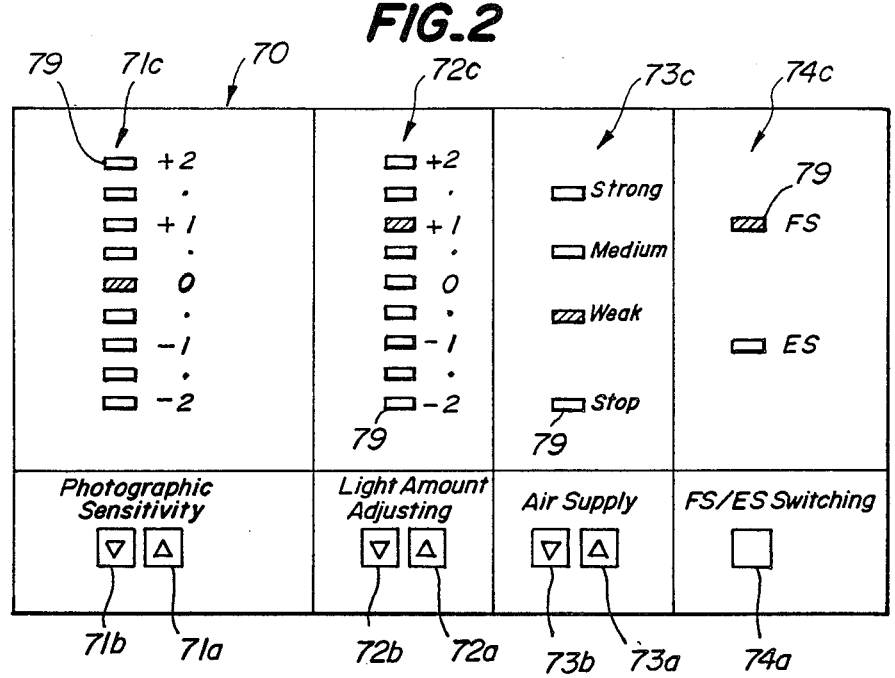
FIG. 2 is a schematic view showing a panel of a light source device of a first embodiment of the present invention.
Figure 3:
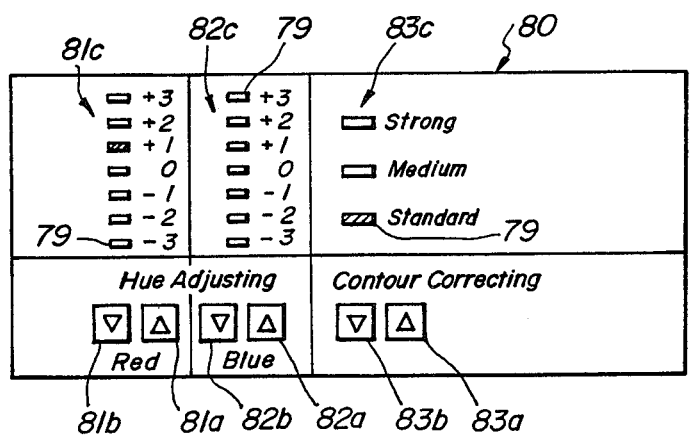
FIG. 3 is a schematic view showing a panel of an image signal processing device.
Figure 4:
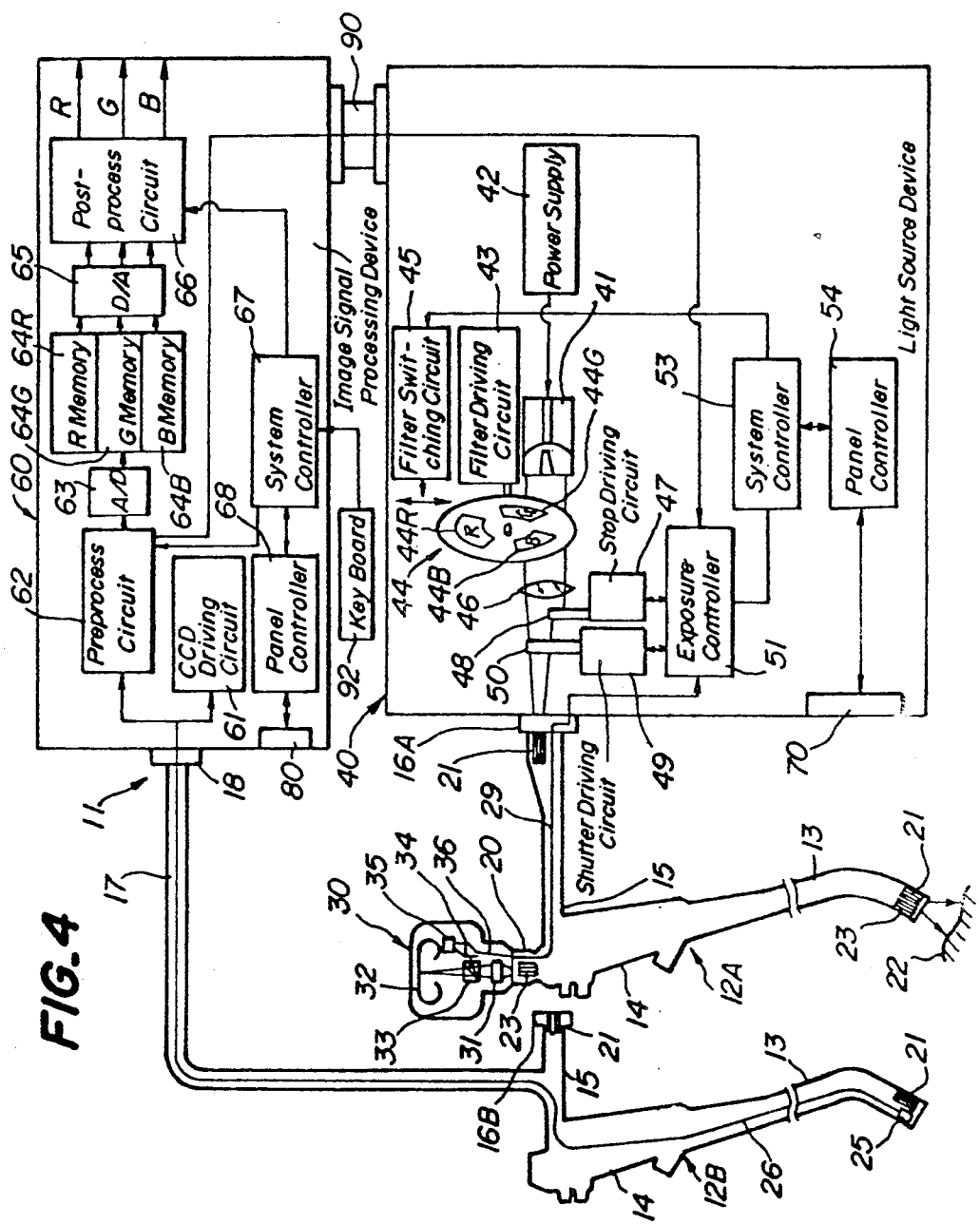
FIG. 4 is a block diagram illustrating the whole system of the endoscope apparatus.

FIGS. 2 to 4 are related to the first embodiment of the present invention. FIG. 2 is a schematic view showing a panel of the light source device, FIG. 3 is a schematic view showing a panel of the image signal processing device, and FIG. 4 is a block diagram for explaining the whole system of the endoscope apparatus.

As shown in FIG. 4, the endoscope apparatus 11 comprises a fiber scope 12A and an electronic scope 12B for use in the field or frame sequential system.

There are also provided a light source device 40, which is commonly used as a control device in both of scopes 12A and 12B, for emitting illumination light for said scopes 12A and 12B, and an image signal processing device 60 in which the signals for the electronic scope 12B are processed. And, said light source device 40 and said image signal processing device 60 are connected to each other via a cable 90.

Said scopes 12A and 12B comprise long, thin and flexible inserting portions 13, and operating portions 14 which are connectively arranged at the end portions of said inserting portions 13, respectively. From said operating portions 14, flexible universal codes 15 are extended, and light source connectors 16A and 16B, which should be connected to said light source device 40, are arranged at the end portions of the respective universal codes 15. From said universal code 15 of the electronic scope 12B, a signal code 17 is also extended and an electric connector 18, which should be connected to said image signal processing device 60, is arranged at the end portion of said signal code 17.

In the fiber scope 12A, there is provided an eyepiece portion 20 at the ed portion of the operating portion 14 thereof, and this eyepiece portion 20 is so arranged that a photographing device 30 can be connected thereto.

In each scopes 12A and 12B, an objective lens system and an illuminating lens (which are not shown in this figure) are arranged at the end portions of the inserting portions 13 thereof. Light guides 21 for transmitting the illuminating light are arranged behind said illuminating lenses, and these light guides 21 are inserted into said inserting portions 13 and are passed through said universal codes 15 up to said light source connectors 16A and 16B. The illuminating light being adapted for the scopes 12A and 12B is generated from said light source device 40 and is guided to the respective incident ends of said light guides 21 when the light source connectors 16A and 16B are connected to said light source device 40. The illuminating light will be transmitted to the end of said inserting portion 13 through said light guides 21 and exited from the exiting ends of said light guides 21 to illuminate objects 22 via the illuminating lenses (not shown).

In said fiber scope 12A, the top end surface of an image guide 23 inserted into, and passed through the inserting portion 13 is arranged at the position that the image is formed by the objective system. The image guide 23 is extended to said eyepiece portion 20 through said inserting portion 13. The image of the object formed at the top end surface of the image guide 23 by said objective system is transmitted to the eyepiece portion 20 through said image guide 23 and will be observed via an eyepiece but not shown.

On the other hand, in said electronic scope 12B, a solid state imaging device, for example, CCD 25 is arranged as an imaging means at the position at which image is formed by the objective system. A signal line 26 is connected to said CCD 25, and the signal line 26 is inserted into, and passed through said inserting portion 13 and said signal code 17 up to said electric connector 18.

Said photographic imaging device 30 to be connected to said eyepiece portion 20 of the fiber scope 12A comprises an imaging lens 31 faced to said eyepiece portion 20 and a film 32 arranged at a plane on which an image is formed by the imaging lens 31. And, a beam splitter 33 is arranged between said imaging lens 31 and said film 32, a light receiving element 34 is arranged at the position that the light flux divided by the beam splitter 33 is received, and the amount of light received by the light receiving element 34 is measured by the control circuit 35. The control circuit 35 is connected to a signal line 29, which is extended from the eyepiece portion 20 to the light source connector 16A in said fiber scope 12A, via a signal line 36. The electric eye (EE) signal supplied from said control circuit 35 is inputted to said light source device 40 via said signal lines 36 and 29.

In the fiber scope 12A, white light is required as illuminating light is required as an illuminating light, on the other hand, in the electronic scope 12B for use in the field or frame sequential system, a sequence of three primary color light etc. are sequentially replaced, is required as an illuminating light. In this embodiment, it is possible to output both of white light and sequential light from the light source device 40.

That is to say, there is provided a lamp for exiting white light, for example, a xenon lamp 41 in the light source device 40. The electric power for the xenon lamp 41 is supplied from the xenon lamp power supply 42. And, on the optical path of said xenon lamp 41, a rotating filter 44 having color transilluminating filters 44R for red color, 44G for green color, and 44B for blue color is arranged in such a manner that the filter 44, which is controlled by a rotating filter driving circuit 43, is freely insertable into or withdrawable from said optical path. Further, said rotating filter 44 is so arranged as to be inserted into or withdrawn from said optical path under the control of a filter switching circuit 45 for selectively inserting the rotating filter into the optical path. And a converging lens 46 is arranged in front of said rotating filter 44 which is serving to collect the light emitted from said xenon lamp 41 and make it incident upon the exiting end of said light guide 21 of said light source connector 16A or 16B. In front of the converging lens 46, a stop 48, which is driven by a stop driving circuit 47, and a shutter 50, which is driven by a shutter driving circuit 49, are successively arranged. Said stop driving circuit 47 and said shutter driving circuit 49 are controlled by an exposure controller 51. The exposure controller 51 serves to receive the electric eye signal measured by said control circuit 35 which is arranged in the imaging device 30 and connected to said eyepiece portion 20 of the fiber scope 12A, and to conduct automatic light control by controlling said stop 48 via said stop driving circuit 47. In said exposure controller 51, said electric eye signal supplied from said control circuit 35 of said imaging device 30 is integrated. When the integrated amount becomes to the predetermined value, the shutter 50 is inserted into the optical path and photographing operation is conducted thereby.

In said light source device 40, a light source device panel 70 is arranged, for example, in front of the housing thereof. A system controller 53 arranged in the light source device 40 drives and controls LEDs arranged on said panel 70 as an indicating means via a panel controller 54, and serves to determine functions to be effected by reading the position of the mode switch arranged on the panel 70.

The light source device panel 70 has a structure as shown in FIG. 2. There are provided an increasing switch 71a, a decreasing switch 71b and an indicator 71c for adjusting photographic sensitivity, an increasing switch 72a, a decreasing switch 72b and an indicator 72c for adjusting the amount of light, an increasing switch 73a, a decreasing switch 73b and an indicator 73c for adjusting the air supply, and a switch 74a and an indicator 74c for switching the modes of fiber scope (FS)/electronic scope (ES).

Out of said adjusting functions, the functions for adjusting the air supply and the amount of light are used for the both of fiber scope 12A and electronic scope 12B, and the function for adjusting the photographic sensitivity is used only for the fiber scope 12A.

The operational condition of each functions is indicated on each indicators 71c, 72c, 73c and 74c by selectively lighting one of the LEDs 79 on each indicators. That is to say, in the indicator 71c for adjusting the photographic sensitivity and the indicator 72c for adjusting the amount of light, the conditions of functions to be adjusted are indicated on the respective nine LEDs 79 arranged upwardly and downwardly. In the indicator 73c for adjusting the air supply, the conditions of strong, medium, weak or stop are indicated on the four LEDs 79, and in the indicator 74c for switching FS/ES (fiber scope/electronic scope), FS or ES is indicated by one of two LEDs 79. When the increasing switches 71a, 72a and 73a are pushed once, the lighted position of LED 79 is moved by one step upwardly, and on the other hand, when the decreasing switches 71b, 72b and 73b are pushed once, the lighted position of LED 79 moves by one step downwardly. The fact that these switches are pushed is read-in by said panel controller 54, and each functions selected thereby are controlled by said system controller 53. For instance, when the increasing switch 71a for adjusting the photographic sensitivity is pushed once, the lightening position of LEDs 79 of the indicator 71c moves by one step upwardly, and when photographing is actually conducted, the exposure controller 51 is controlled so that the exposure degree is increased by one step. Also, when the switch 74a for switching FS/ES mode is pushed once, the lightening position of LEDs 79 on the indicator 74c moves to the other position.

In case that the fiber scope mode is selected, said rotating filter 44 is removed from the optical path via the filter switching circuit 45, all LEDs on panel 70 relating to only the electronic scope are switched off and the switches relating thereto are made inoperative under the control of said system controller 53. In this embodiment, the indicators and switches relating to only the electronic scope are not provided, and therefore there is no LEDs to be switched off. The exposure controller 51 is also switched so as to receive the electric eye signal supplied from the imaging device 30 under the control of the system controller 53.

On the other hand, in case that the electronic scope is selected, said rotating filter 44 is inserted into the optical path via the filter switching circuit 45, the LEDs on the panel 70 relating only to the fiber scope are switched off and the switches relating thereto are made inoperative under the control of said system controller 53. In this embodiment, all LEDs of the indicator 71c for adjusting the photographic sensitivity are switched off and the switches 71a, 71b and the shutter driving circuit 49 are made inoperative. And the exposure controller 51 is switched on so as to receive the light control signal supplied from a preprocess circuit 62 (stated later) arranged in the image signal processing device 60.

The lightening LEDs 79 are denoted by hatchings in the figure.

On the other hand, said image signal processing device 60 comprises a CCD driving circuit 61 for driving said CCD 25, which is arranged at the end portion of said electronic scope 12B, as shown in FIG. 4. The image signal read out by the CCD 25, which is driven by the CCD driving circuit 61, is supplied to said preprocess circuit 62 to make the hue correction and $\gamma$ correction. And thereafter the processed signals are supplied to an A/D converter 63 to convert the signals from analogue to digital. And the digital image signals $\gamma$ converted by said A/D converter is written-in an R frame-memory 64R, a G frame-memory 64G and a B frame-memory 64B, successively, in synchronized with the switching of the illuminating light. The image signals written in said each frame memories 64R, 64G and 64B are read out simultaneously and converted to analogue signals by a D/A converter 65 and supplied to a post process circuit 66. In this post process circuit 66, the signals are processed in such manner that the contour of image is emphasized and character signals supplied from a key board 92 are superimposed via a system controller 67. And the processed signals are supplied to the external monitor (not shown) as an R, G and B image signals.

That is to say, the functions of the hue or $\gamma$ correction conducted in said preprocess circuit 62 or the function of the contour emphasizing or superimposing conducted in said post process circuit 66 are controlled by the system controller 67.

In said image signal processing device 60, there is provided an image signal processing device panel 80 at the front surface of the housing thereof. Said system controller 67 drives and controls the LEDs, which are provided on the panel 80 for indicating the mode of the apparatus, via a panel controller 68, and changes the modes of various kinds of functions by reading the positions of the switches provided on the panel 80. That is to say, the hue correcting and the contour emphasizing are conducted via the panel controller 68 and the system controller 67 to such an extent which has been set by the hue and the contour control switches provided on said panel 80.

And, the light control signal obtained at the preprocess circuit 62 is supplied to said exposure controller 51 arranged in said light source device 40 via said cable 90.

Said image signal processing device panel 80 has a structure as shown in FIG. 3. In said image signal processing device panel 80, there are provided an increasing switch 81a, a decreasing switch 81b and an indicator 81c for adjusting the red color hue, an increasing switch 82a, a decreasing switch 82b and an indicator 82c for adjusting the blue color hue, an increasing switch 83a, a decreasing switch 83b and an indicator 83c for adjusting the contour, respectively. In each indicators 81c, 82c and 83c, the operational condition of each functions is indicated by selectively lighting one of LEDs thereon. That is to say, in the indicators 81c for adjusting the red color hue and 82c for the blue color hue, the operational condition of each adjusting functions is indicated by seven LEDs 79 arranged up- and down-wardly on the indicators 81c and 82c. In the indicator 83c for adjusting the contour, each condition of strong, medium and standard is indicated by three LEDs arranged up- and down-wardly thereon. And, when each increasing switch is depressed once, the lightening LED 79 corresponding thereto moves up by one step, and when each decreasing switch is pushed once, the lightening LED 79 corresponding thereto moves down by one step. The fact that each switch is pushed is read by said panel controller 68 via said system controller 67 and each functions are controlled in accordance with the operational conditions represented by the lightening indicators.

The following explanation is about the operation of the present embodiment.

In case of using the fiber scope 12A, the fiber scope 12A is connected to the light source device 40, and the fiber scope mode is selected by selecting the switch 74a for switching FS/ES mode arranged on the light source device panel 70 of the light source device 40. The fact that the fiber scope mode is selected by the switch 74a is detected by the panel controller 54 and the detected information is supplied to the system controller 53.

Under the control of the system controller 53, the rotating filter 44 is taken off from the optical path via the filter switching circuit 45, the LEDs 79 on the indicators of the functions relating only to the electronic scopes are switched off and the related switches are made inoperative. However, in this embodiment, there is no indicator and switches for the functions relating only to the electronic scope. And, the exposure controller 51 is switched so as to receive the electric eye signal supplied from the photographing device 30 under the control of the system controller 53.

The white light exited from the lamp 41 arranged in said light source device 40 is converged at the converging lens 46 without passing through the rotating filter 44 and is made incident upon the incident end of the light guide 21 arranged in the light source connector 16A of the fiber scope 12A. This white illuminating light is introduced to the top end portion of the inserting portion 13 through the light guide 21 and exited therefrom to illuminate the object 22.

The reflecting light reflected from the object 22 is imaged at the top surface of the image guide 23 by the objective lens system not shown. The image of the object is transmitted to the eyepiece portion 20 through the image guide 23 and observed thereat. And, since the photographing device 30 is connected to said eyepiece portion 20, the image of the object can be photographed.

When the fiber scope 12A is used, the mode of each functions for adjusting the amount of light and the air supply are changed by that the switches 72a or 72b and 73a or 73b corresponding to each functions are pushed. And when said photographing device 30 is used, the exposure is adjusted by that the switches 71a and 71b for adjusting the photo imaging sensitivity are pushed. Each operational condition of the functions for adjusting the photographing sensitivity, the amount of light and the air supply is indicated by means that the LEDs on the indicators 71c, 72c and 73c which are corresponding to said each functions are lighted.

Also, when photographing is conducted by means of said photographing device 30, the exposure controller 51 receives the electric eye signal measured at the control device 35 arranged in the photographing device 30 and automatic light control is conducted by controlling the stop 48 via the stop driving circuit 48. Also, at the exposure controller 51, the electric eye signal supplied from the control circuit 35 is integrated and when the integrated amount becomes to the predetermined amount the shutter 50 is inserted into the optical path. In this manner the photographing can be conducted.

On the other hand, in case that the electronic scope 12B is used, the light source connector 16B thereof is connected to the light source device 40, and the electronic connector 18 is connected to the image signal processing device 60. And the electronic scope mode is selected by the switch 74a for switching FS/ES mode arranged on the light source device panel 70. The fact that the electronic scope mode is selected is read in the panel controller 54. Under the control of the system controller 53, the rotating filter 44 is inserted into the optical path via the filter switching circuit 45, the LEDs 79 on the indicators of the functions on the panel 70 relating only to the fiber scope are switched off and the switches thereon are made in operative. In this embodiment, all of LEDs on the indicator 71 for adjusting photographic sensitivity are switched off and the switches 71a and 71b therefor are made inoperative. And the shutter driving circuit 49 is also made inoperative, for example, by cutting off the power supply thereto. And the exposure controller 51 is switched so as to receive the light control signal supplied from the preprocess circuit 62 arranged in the image signal processing device 60.

The white light exited from the lamp 41 arranged in the light source device 40 is passed through the rotating filter 44 and thus becomes to be the sequential light by which the field is sequentially changed in the order of R, G, B. The sequential light is converged at the converging lens 46 and made incident upon the incident end of the light guide 21 arranged in the light source connector 16B of the electronic scope 12B. This illuminating light is introduced to the top end portion of the inserting portion 13 through the light guide 21, and exited from the top surface thereof to illuminate the object 22.

The reflecting light of the sequential illuminating light reflected from the object is imaged on the CCD 25 by means of the objective lens system not shown. This CCD 25 is driven by the CCD driving circuit 61 and the image signal read out thereby is supplied to the external monitor (not shown) as, for example, R-, G-, B- image signals via the preprocess circuit 62 and postprocess circuit 66.

When using the electronic scope 12B, the condition or degree of each functions for adjusting the amount of light and the air supply is changed by pushing the switches 72a, 72b, 73a and 73b on the light source device panel 70 which are corresponding to each functions. And, the operational mode of those functions are indicated by lighting the LEDs 79 on the indicators 72c and 73c corresponding thereto. The condition of each functions for adjusting the hue and correcting the contour is changed by pushing the switches 81a, 81b, 82a, 82b, 83a and 83b on the image signal processing device panel 80 corresponding thereto. And the operational condition of those functions are indicated by lighting the LEDs 79 of of the indicators 81c, 82c and 83c corresponding thereto.

The exposure controller 51 arranged in the light source device 40 receives the light control signals supplied from the preprocess circuit 62 arranged in the image signal processing device 60, nd controls the stop 48 on the basis of the amount of light received in the electronic scope via said stop driving circuit 47, so that the light control can be conducted automatically.

As described above, in this embodiment, in the light source device panel 70, only the LEDs on the indicators indicating the functions relating to the fiber scope 12A are lighted during the fiber scope 12A is used, and only the LEDs on the indicators indicating the functions relating to the electronic scope are lighted during the electronic scope 12B is used. In the other words, the LEDs of indicators for the unnecessary functions are always cut off. Therefore the operator can easily distinguish only the necessary functions and thus the operativeness will be increased.

Further, since the switches for unnecessary functions are made inoperative, the misoperations can be avoided.

Moreover, when the electronic scope 12B is used, since the unnecessary functions, i.e., the shutter driving circuit 49 are made inoperative, for example, by cutting off the power supply of this circuit 49, the electric energy consumption can be decreased.

Figure 5:
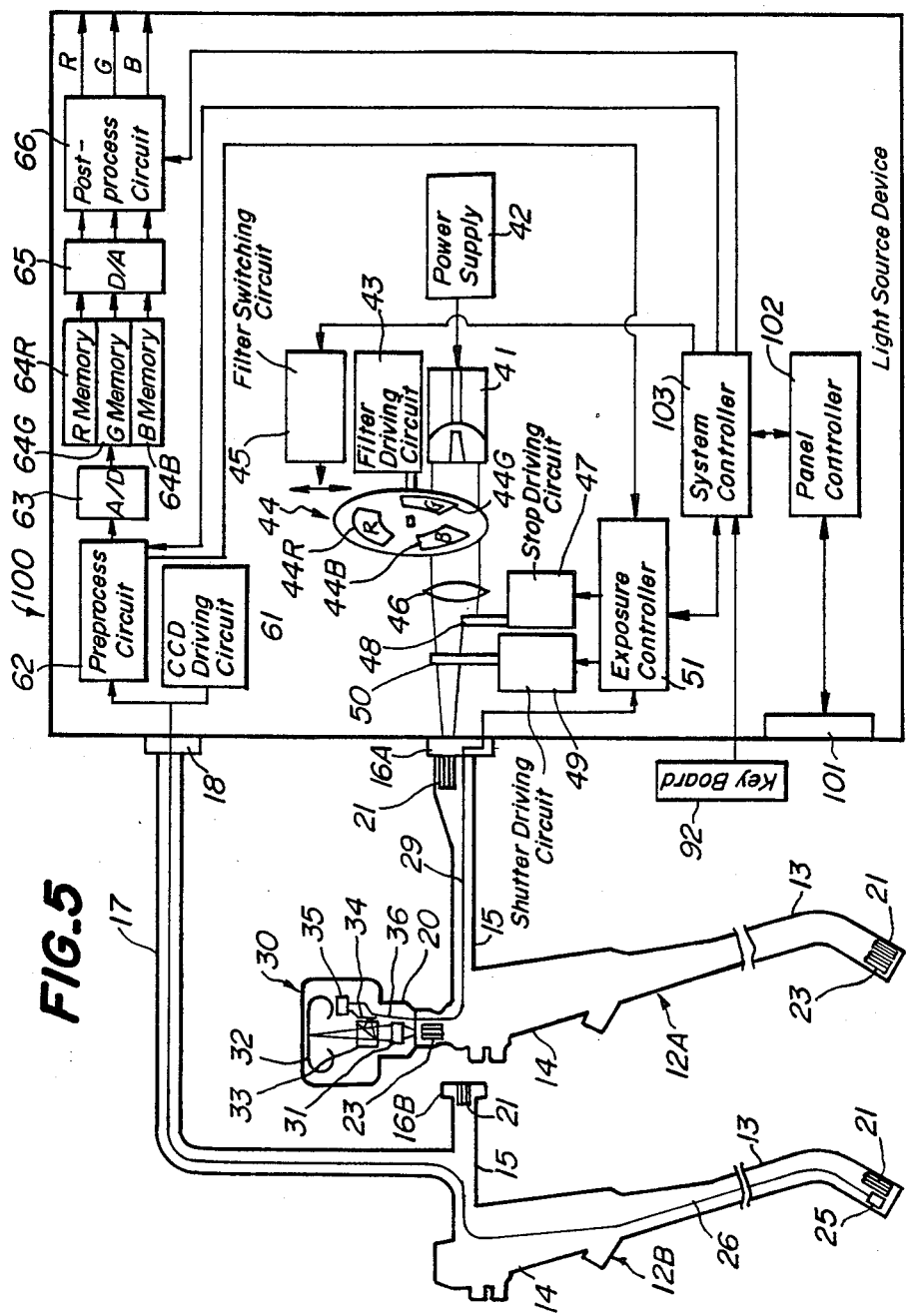
FIG. 5 is a block diagram indicating the whole system of second embodiment of the endoscope apparatus, according to the invention.
Figure 6:
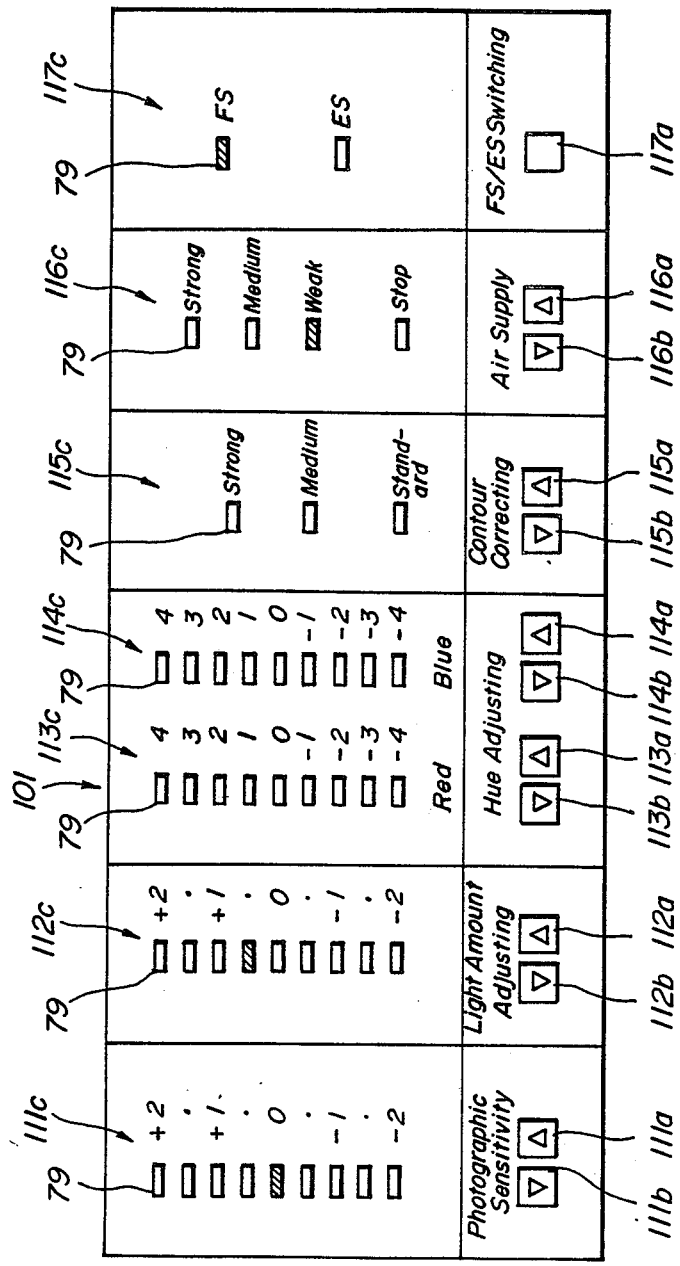
FIG. 6 is a schematic view of a panel of a light source device thereof.

FIGS. 5 and 6 are related to the second embodiment of the present invention, FIG. 5 is a schematic view showing the structure of the endoscope apparatus as a whole and FIG. 6 is a schematic view illustrating the light source device panel thereof.

In this embodiment, there is provided a light source device 100 in which light source device 40 and image signal processing device 60 are arranged.

In said light source device 100, a light source device panel 101, in which the light source device panel 70 and the image signal processing panel 80 in the first embodiment are integrated, is arranged, for example, in front of the housing thereof. And, a panel controller 102, in which the panel controllers 54 and 68 in the first embodiment are integrated, and a system controller 103, in which the system controllers 53 and 67 in the first embodiment are integrated, are provided in said light source device 100. Said system controller 103 drives and controls LEDs arranged on said light source device panel 101 as an indicating means and serves to switch the operational condition of various kinds of functions of the apparatus by reading the signals supplied from the switches arranged on the light source device panel 101 as an operational condition changing means.

Said light source device panel 101 has a structure as shown in FIG. 6. That is to say, there are provided an increasing switch 111a, a decreasing switch 111b and an indicator 111c for adjusting the photo imaging sensitivity, an increasing switch 112a, a decreasing switch 112b and indicator 112c for adjusting the amount of light, an increasing switch 113a, a decreasing switch 113b and an indicator 113c for adjusting the red color hue, an increasing switch 114a, a decreasing switch 114b and an indicator for adjusting the blue color hue, an increasing switch 115a, a decreasing switch 115b and an indicator 115c for correcting the contour, an increasing switch 116a, a decreasing switch 116b and an indicator 116c for adjusting the air supply, and a switch 117a and an indicator 117c for switching the FS and ES mode, respectively.

Out of each adjustable functions provided in said light source device panel 101, the function for adjusting the photographing sensitivity is only for use in the fiber scope, the functions for adjusting the hue and correcting the contour are only for use in the electronic scope, and the functions for adjusting the amount of light and the air supply are for use in both of scopes. The other structure of this light source device 101 is same as the first embodiment.

In this embodiment, in case that the fiber scope 12A is connected to the light source device 100, the FS mode is selected by means of the switch 117a for switching the mode of FS/ES arranged on the panel 101. This selected mode is read-in by the panel controller 102, and the following processing is conducted in the system controller 103.

That is to say, by means of the system controller 103, the rotating filter 44 is taken off from the optical path via the filter switching circuit 45, all LEDs 79 of the indicators on the panel 101 indicating the functions related only to the electronic scope are switched off, and the switches for the functions related only to the electronic scope are made inoperative. In this embodiment, all LEDs 79 in the indicators 113c, 114c and 115c indicating the functions for adjusting the hue and correcting the contour are switched off and switches 113a, 113b, 114a, 114b, 115a and 115b therefor are made inoperative. The exposure controller 51 is switched to receive the electric eye signals supplied from the photographing device 30. Thus, the automatical light control is effected in accordance with the level of the electric eye signal representing the amount of light measured in the photographing device 30. Further, in said light source device 100, the functions relating only to the electronic scope, i.e. the pre-process circuit 62, CCD driving circuit 61, the A/D converter 63, the frame memory 64R, 64G and 64B, D/A converter 65 and the postprocess circuit 66 etc., are made inoperative by, for example, cutting off the power supply thereto.

On the other hand, in case that the electronic scope 12B is adapted to the light source device 100, the light source connector 16B and the electric connector 18 of the electronic scope 12B are connected to the light source device 100, and the electronic scope mode is selected by means of the switch 117a for switching the FS and ES mode arranged on the light source device panel 101. The selected mode is read in the panel controller 102 and the following processing is conducted under the control of the system controller 103.

That is to say, the rotating filter 44 is inserted into the optical path via the filter switching circuit 45, all of the LEDs in the indicators on the panel 70 indicating the functions relating only to the fiber scope are switched off and the related switches are made inoperative. In this embodiment, all LEDs of the indicator 111c for adjusting the photographing sensitivity are switched off and the switches 111a and 111b therefor are made inoperative. Also, the exposure controller 51 is switched to receive the light control signal supplied from the preprocess circuit 62. Therefore, the automatic light control is carried out in accordance with the amount of light received by the CCD 25. And, the light source device 100, the function related only to the fiber scope, i.e. the shutter driving circuit, is made inoperative by cutting off the power supply therefor.

According to the present embodiment, in the light source device panel 101, when the fiber scope 12A is used, only the LEDs 79 of the indicators indicating the functions related to the fiber scope 12A are lighted, and when the electronic scope 12B is used, only the LEDs 79 of the indicators indicating the functions related to the electronic scope 12B are lighted. And therefore, since the indicators for the unnecessary functions are cut off, and the switches related thereto are made inoperative, the mis-operations are avoided and the operativeness will be increased.

Further, during the electronic scope is used, the unnecessary function, i.e. the shutter driving circuit 49 is made inoperative by cutting off the power supply, and during the fiber scope 12A is used, the unnecessary functions, i.e. the CCD driving circuit 61 and the signal processing circuit from the pre-process circuit 62 to the post-process circuit 66 are made inoperative by cutting off the power supply, so that the electric power consumption will be decreased. The other functions and effects of this embodiment are same as those of the first embodiment.

Figure 7:
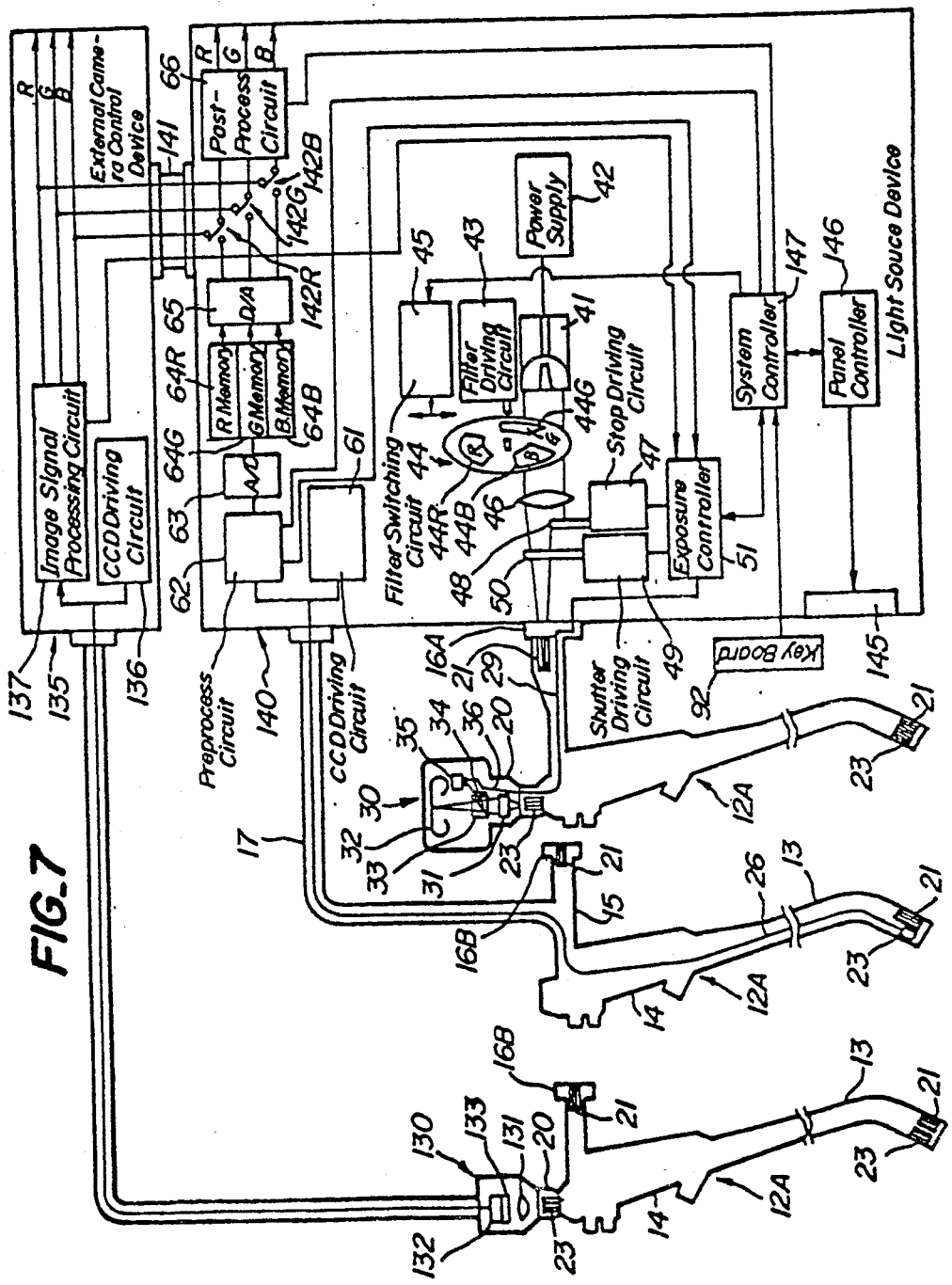
FIG. 7 is a block diagram illustrating the whole system of a third embodiment of the present invention.
Figure 8:
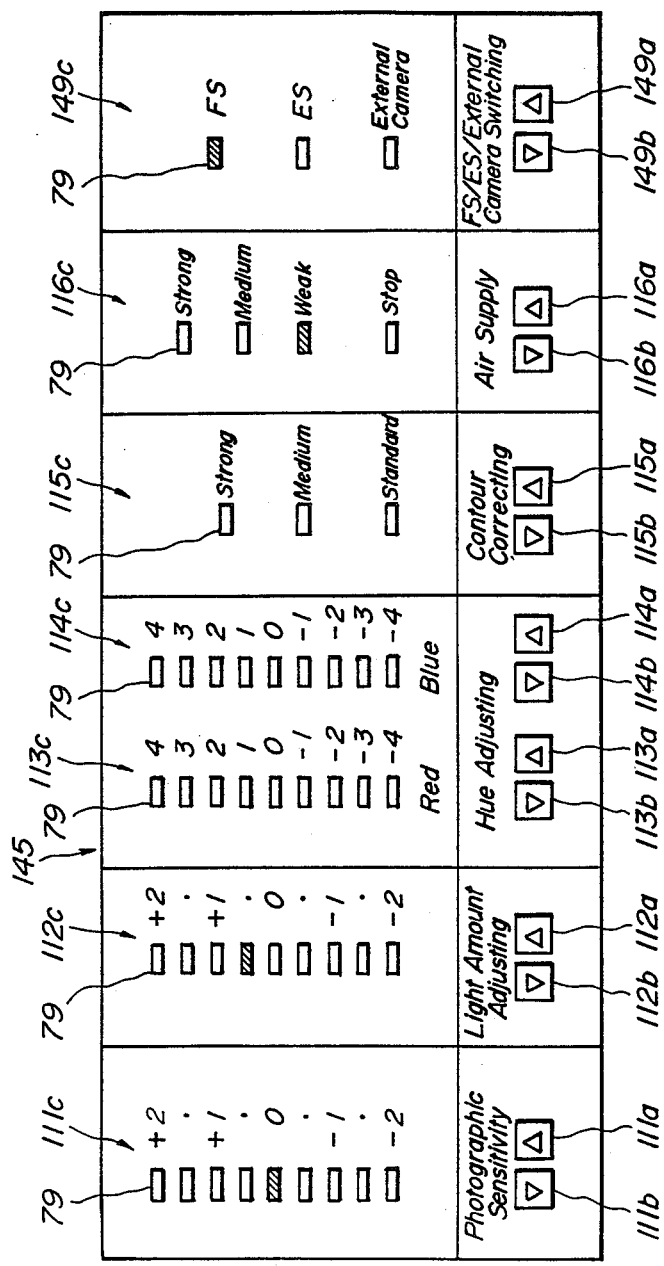
FIG. 8 is a schematic view showing a panel of a light source device thereof.

FIGS. 7 and 8 show the third embodiment of the control apparatus according to the present invention, and FIG. 7 is a schematic view showing the structure of the endoscope apparatus as a whole, and FIG. 8 is a schematic view illustrating the light source device panel thereof. In this embodiment, as shown in FIG. 7, an external television camera 130 to which the simultaneous system is adapted (hereinafter external camera) is connected to the eyepiece position 20 of the fiber scope 12A, and thus the image taken by the fiber scope 12A can be observed on the monitor by the external camera.

The external camera 130 comprises an imaging lens 131 which is faced to the eyepiece portion 20 of the fiber scope 12A and a solid state imaging device, for example, a CCD 132, which is arranged on the image plane of the imaging lens 131. On the front surface of said CCD 132, a color filter array 133, in which color filters of R, G, B are arranged in mosaic, is provided. Therefore, white light is necessary as an illuminating light when said external camera is used.

Said external camera 130 is connected to an external camera control device 135. And the CCD 132 arranged in the external camera 130 is driven by a CCD driving circuit 136 provided in the external camera control device 135. The image signal read out by the CCD driving circuit 136 is processed by an image signal processing circuit 137 arranged in said external camera control device 135 and is converted to the R, G or B signals which are supplied to the monitor.

On the other hand, the light source device 140 of the present embodiment has the structure same as that of the second embodiment, but the device 140 is connected to said external camera control device 135 via a cable 141. There are provided switches 142R, 142R and 142B having two point contacts for each signals R, G and B between the D/A converter 65 and the postprocess circuit 66. Thus, the signal supplied from said D/A converter 65 and the signal supplied from the image signal processing circuit 137 in said external camera control device 135, which is inputted via said cable 141, are alternatively switched thereby to be inputted in the post-process circuit 66. In the postprocess circuit 66, various signal processings such that the contours are emphasized or the character signal inputted by the keyboard 92 are superimposed can be conducted. The light control signals supplied from said image signal processing circuit 137 is inputted into said exposure controller 51 which is arranged in the light source device 140 via said cable 141.

In said light source device 140, a light source device panel 145 is provided, for example, at the front surface of the housing thereof, and a panel controller 146 and a system controller 147 are also provided in the device 146. In said system controller 147, the LEDs, which are provided on said light source device panel 145 as the indicating means, are driven and controlled thereby via said panel controller 146, and the conditions of various kinds of functions are changed by reading in the mode of the switches on said light source device panel 145 provided as the operational condition changing means.

As shown in FIG. 8, said light source device panel 145 has almost the same structure as the light source device panel 101 of the second embodiment. However, an increasing switch 149a, a decreasing switch 149b and an indicator 149c for switching FS/ES/external camera mode are provided instead of the switch 117a and the indicator for switching FS/ES of the second embodiment. In the indicator 149c, there are provided three LEDs 79 arranged up- and down-wardly one of which is for fiber scope (FS) other one of which is for electronic scope and another one of which is for external camera. When said increasing switch 149a is pushed once, the lightening position of LEDs 79 of said indicator 149c moves by one step upwardly, and when said decreasing switch is pushed once, the lightening position of LEDs 79 moves by one step downwardly.

Out of the adjustable functions provided in said light source device panel 145, the function for adjusting the photographic sensitivity is only for use in the photographing device 30 connected to the fiber scope 12A, the function for adjusting the hue is only for use in the electronic scope 12B, the function for emphasizing the contour is for use in the electronic scope 12B or in the external camera with the fiber scope 12A, and the functions for adjusting the amount of light and the air supply is for use in all cases.

In this embodiment, in case that the fiber scope 12A is used, the fiber scope 12A is connected to the light source device 140, and the fiber scope mode is selected by means of the switches 149a, 149b provided on the light source device 140 for switching FS/ES/external camera mode. The selected mode is read in by the panel controller 146, and the same processing as the case that the mode of fiber scope is selected in the second embodiment is conducted under the control of the system controller 147.

On the other hand, in case that the electronic scope 12B is used, the light source connector 16B and the electric connector 18 of the electronic scope 12B are connected to the light source device 140, and the electronic scope mode is selected by means of the switches 149a, 149b for switching FS/ES/external camera mode. The selected electronic scope mode is read in by the panel controller 146, and the same processing as the case that the mode of electronic scope is selected in the second embodiment is performed by means of the system controller 147.

And, in case that the fiber scope 12A with the external camera 130 is used, the fiber scope 12A is connected to the light source device 140, and the external camera 130 is connected to the external camera controlling device 135. And also, the external camera mode is selected by means of the switches 149a, 149b for switching FS/ES/external camera mode. The selected mode of external camera is read by the panel controller 146, and the proceedings are conducted under the control of the system controller 147 such that the rotating filter 44 is taken off from the optical path via the filter switching circuit 45, all LEDs 79 on the indicators on the panel 145 indicating the functions related not to the external camera are switched off and the switches therefor are made inoperative. In this embodiment, the LEDs on the indicators 111c, 113c and 114c indicating the functions for adjusting the photographing sensitivity and the hue are switched off, and the switches 111a, 111b, 113a, 113b, 114a and 114b therefor are made inoperative. And the exposure controller 51 is switched so as to receive the light control signal supplied from the image signal processing circuit 137 which is arranged in the external camera control device 135. Therefore, the automatic light control is conducted in accordance with the amount of light measured at the CCD 132 provided in the external camera 130. And the unnecessary functions for using the external camera, i.e. the shutter driving circuit 49, the CCD driving circuit 61, the pre-processing circuit 62, and the processing circuits for the A/D converter 63, the frame memories 64R, 64G, 64B and D/A converter are made inoperative, for example, by cutting off the power supply therefor.

According to the present embodiment, the LEDs on the light source device panel 145 indicating the functions necessary for each operational modes of observing by naked eye by using the fiber scope 12A, photographing by using the fiber scope 12A and the imaging device connected thereto, using the electronic scope 12B, or observing on the monitor by using the fiber scope 12A and the external camera 130 thereto are lighted, the other LEDs indicating the unnecessary functions are cut off, and the switches for the unnecessary functions are made inoperative, and thus misoperation can be avoided and the operativeness will be increased as well as the first embodiment.

Since the power supply for the unnecessary functions is cut off, the electric power consumption will be decreased.

The other functions and effect according to this embodiment are same as the first embodiment.

Figure 9:
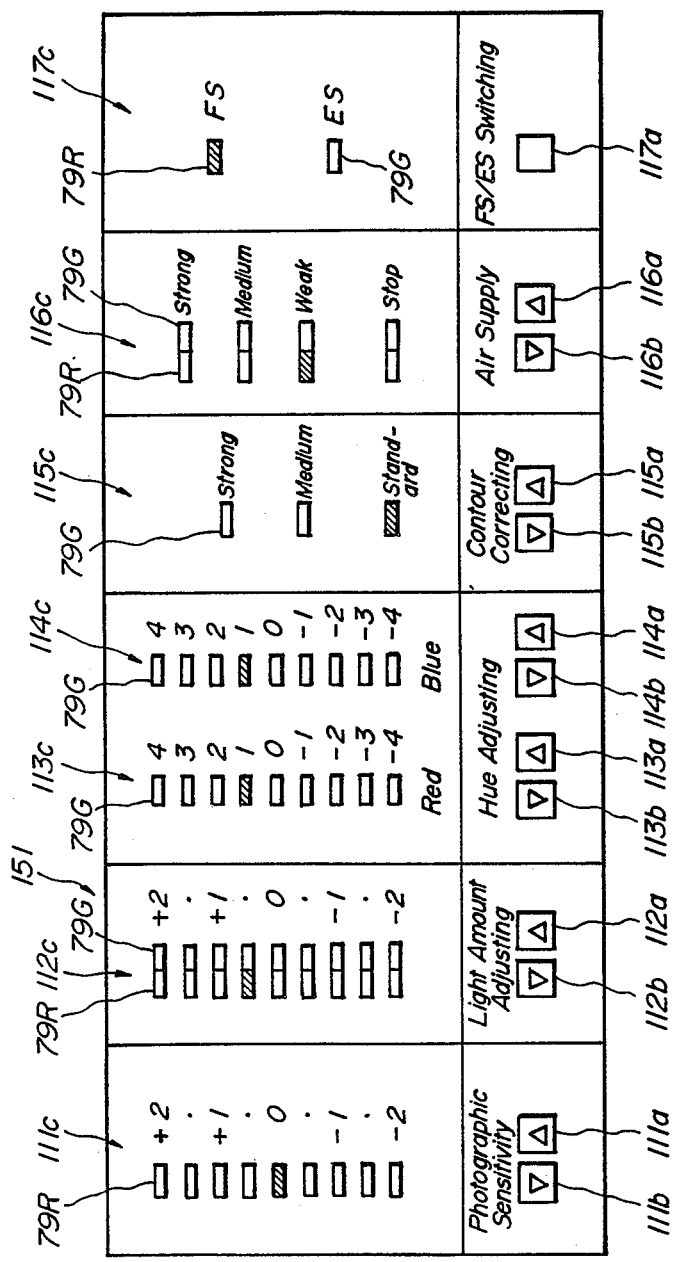
FIG. 9 is a schematic view showing a panel of a light source device according to a fourth embodiment of the present invention.

FIG. 9 is a schematic view showing the light source device panel according to the fourth embodiment of the present invention. The light source device panel 151 according to the fourth embodiment has almost the same structure as the light source device panel 101 of the second embodiment. However, in this embodiment, the color of the LEDs on the indicators indicating the functions for the fiber scope is made different from that for the for the electronic scope. That is to say, the red illuminating LEDs 79R are used in the indicator 111c for adjusting the photographic sensitivity which is used only for the fiber scope, and the green illuminating LEDs 79G are used in the indicators 113c 114c and 115c for adjusting the hue and correcting the contour which are used only for the electronic scope. And there are provided both of the red illuminating LEDs 79R and the green illuminating LEDs 79G on the indicators 112c and 116c for the functions for adjusting the amount of light and the air supply which are used for the both scopes. And, when the fiber scope is used, only the red illuminating LEDs 79R are lighted and when the electronic scope is used, only the green illuminating LEDs 79G are lighted. On the indicator 117c for switching FS/ES mode, a red illuminating LED 79R is used for indicating the fiber scope mode and a green illumination LED 79G is used for indicating the electronic scope mode.

In this embodiment, it is not necessary to switch off all of the LEDs 79R or 79G indicating the mode of the unnecessary functions.

According to this embodiment, since it is possible to distinguish the fiber scope mode or the electronic scope mode by means of the color of LEDs indicating each functions, the mis-operation can be prevented.

FIG. 10 is a schematic view illustrating the light source device panel according to the fifth embodiment of the present invention.

The light source device panel 161 has almost the same structure as the light source device panel 101 of the second embodiment. However, the shapes of the illuminating portions of LEDs for the fiber scope and for the electronic scope are made different from each other. That is to say, the LEDs 79S having the star-shaped illuminating portion are used for the indicator 111c indicating the function for adjusting the photographing sensitivity which is used only for the fiber scope, and the LEDs 79C having the circle-shaped illuminating portion are used for the indicator 113c, 114c and 115c indicating the functions for adjusting the hue and correcting the contour which are used only for the electronic scope. There are provided both of the star-shaped LEDs 79S and the circle-shaped LEDs 79C on the indicators 112c and 116c indicating the functions for adjusting the amount of light and the air supply which are used in both scopes. And, when the fiber scope is used, the star-shaped LEDs 79S are lighted, and when the electronic scope is used, the circle-shaped LEDs 79C are lighted. Further, on the indicator 117c for switching FS/ES mode, the star-shaped LED 79S is used for indicating the fiber scope mode and the circle-shaped LED 79C is used for indicating the electronic scope mode.

In this embodiment, there is not necessary to cut off the unnecessary LEDs on the indicators.

According to the present embodiment, it is possible to distinguish which mode of the fiber scope or the electronic scope is now adapted by means of the shape of LED on the indicators, and thus the misoperation can be avoided.

The light source device panels according to the fourth and fifth embodiments have almost the same structure as that of the second embodiment, but only the color or shape of the indicating portions is different therefrom. In the same manner, it may be possible to make the color or shape of LEDs on the panel of the other embodiments different from each other. For instance, in the light source device panel 145 of the third embodiment, it may be possible to arrange that the color or the shape of LEDs are made difference from each other corresponding to the mode of fiber scope, electronic scope or external camera.

It should be noted that the present invention is not limited to the embodiments explained above, but many modifications may be conceived by those skilled in the art within the scope of the invention. For instance, it may be possible to arrange that the mode is distinguished by means that the LEDs for the necessary functions are illuminated brightly and the LEDs for the unnecessary functions are illuminated in dark, instead that the LEDs for the unnecessary functions are switched off.

And, in the endoscope apparatus in which the light source device and the image signal processing device are separately provided, the panel serving as the indicating means and the mode changing means is not limited to the panel arranged on the light source device, for example, it may be possible to use the panel arranged on the image signal processing device.

It may be also possible to provide a distinguishing means for distinguishing the kind of scopes being connected to the light source device, so that the functions for the selected scope are automatically switched and adapted thereto.

Furthermore, the present invention can be adapted not only to the control device which is commonly used in the fiber scope and the electronic scope but also to the control device which is commonly used in the electronic scope using the field or frame sequential system and the electronic scope using the simultaneous system, in which the functions to be used are different from each other.

As described above, according to the present invention, the operational condition of each functions in the control means is indicated in the mutually distinguishable manner in accordance with the kind of endoscope to be used, and furthermore, only the condition switching means for the functions which are necessary for the endoscope in use are made operative. Therefore, there are advantages that the mis-operating can be prevented and the operativeness will be increased.

What is claimed is:

1. The control apparatus for endoscopes according to the present invention comprising:
    a controlling means for controlling plural kinds of functions which are at least partially different for each of said plural kinds of endoscopes;
    a selecting means for selecting at least one function to be controlled out of said plural kinds of functions in accordance with an endoscope connected to said control apparatus;
    an adjusting means for adjusting an operational condition of said function selected by said selecting means; and
    an indicating means for indicating the operational condition of said function selected by said selecting means so as to be able to distinguish said function from at least one function which is not selected by said selecting means.

2. An apparatus according to claim 1, wherein said adjusting means comprises a plurality of adjusting members each corresponding to respective functions and wherein at least one adjusting member corresponding to at least one function which is not selected by said selecting means is made inoperative.

3. An apparatus according to claim 2, wherein said selecting means has a switch which is operated manually by an operator.

4. An apparatus according to claim 3, wherein said selecting means includes an indicator for indicating the kind of endoscope which is connected to said control apparatus and is denoted by said switch.

5. An apparatus according to claim 4, wherein said switch has a first position to select a fiber scope and a second position to select a electronic scope.

6. An apparatus according to claim 4, wherein said indicating means has a plurality of indicators each corresponding to respective functions, each of said indicators has a plurality of illuminating elements which are selectively driven in accordance with the operational condition which is set by said adjusting means, and all of said illuminating elements on at least one indicator corresponding to at least one function which is not selected by said selecting means are made inoperative.

7. An apparatus according to claim 4, wherein
    said indicating means has a plurality of indicators each corresponding to respective functions, each of these indicators has a plurality of illuminating elements which are selectively driven in accordance with the operational condition which is set by said adjusting means, and the illuminating elements of the indicators corresponding to said function of endoscope set by said switch are lighted in the same fashion as the indicator indicating the kind of said endoscope on the indicator of said selecting means.

8. An apparatus according to claim 7, wherein
    at least one of said indicators of said indicating means is so arranged that the operational condition of at least one function which is commonly used for plural kinds of endoscopes can be indicated in a plurality of indicating fashions corresponding to a plurality kinds of endoscopes.

9. An apparatus according to claim 8, wherein:
    the indicator of said selecting means distinguishes a plurality of endoscopes by means of different colors of light, and the indicators indicating the operational condition in a plurality of indicating fashions in said indicating means has a plurality of arrays of illuminating elements emitting different colors light which are corresponding to said different colors light indicated on the indicator of said selecting means.

10. An apparatus according to claim 8, wherein
    said indicators of said indicating means distinguish a plurality of endoscopes by means of lights having different shapes, and the indicators indicating the operational conditions in a plurality of indicating fashions of said indicating means has a plurality of arrays of illuminating elements emitting light having different shapes corresponding to said light having different shapes indicated on the indicator of said selecting means.

11. An apparatus according to claim 2 further comprising means for distinguishing the kind of endoscope connected to said control apparatus and for automatically operating said selecting means in accordance with the kind of endoscope connected to said control apparatus.

12. An apparatus according to claim 2 wherein said selecting means has a switch is automatically operated in accordance with the type of endoscope connected to said control apparatus.

* * * * *